United States Patent
Brown et al.

(10) Patent No.: US 11,278,352 B2
(45) Date of Patent: Mar. 22, 2022

(54) PROTECTIVE CAPS OF TIPS FOR SURGICAL LASER FIBERS

(71) Applicant: Joe D. Brown, Panama City Beach, FL (US)

(72) Inventors: Joe D. Brown, Panama City Beach, FL (US); Daniel Malphurs, Panama City Beach, FL (US); Howard S. Klymas, Panama City Beach, FL (US)

(73) Assignee: OPTICAL INTEGRITY, INC., Panama City Beach, FL (US)

( * ) Notice: Subject to any disclaimer, the term of this patent is extended or adjusted under 35 U.S.C. 154(b) by 665 days.

(21) Appl. No.: 16/098,962

(22) PCT Filed: May 4, 2017

(86) PCT No.: PCT/US2017/031091
§ 371 (c)(1),
(2) Date: Nov. 5, 2018

(87) PCT Pub. No.: WO2017/192869
PCT Pub. Date: Nov. 9, 2017

(65) Prior Publication Data
US 2019/0083177 A1    Mar. 21, 2019

Related U.S. Application Data

(60) Provisional application No. 62/465,407, filed on Mar. 1, 2017, provisional application No. 62/399,677, filed on Sep. 26, 2016, provisional application No. 62/336,888, filed on May 16, 2016, provisional application No. 62/332,285, filed on May 5, 2016.

(51) Int. Cl.
    *A61B 18/26*    (2006.01)
    *A61B 1/018*    (2006.01)
    *A61B 18/22*    (2006.01)
    *G02B 6/44*     (2006.01)
    (Continued)

(52) U.S. Cl.
    CPC ............ *A61B 18/26* (2013.01); *A61B 1/0008* (2013.01); *A61B 1/00137* (2013.01); *A61B 1/018* (2013.01); *A61B 18/22* (2013.01); *G02B 6/44* (2013.01); *G02B 6/443* (2013.01); *G02B 6/4415* (2013.01); *G02B 6/4479* (2013.01); *G02B 6/4486* (2013.01); *A61B 2018/00511* (2013.01); *A61B 2018/00625* (2013.01)

(58) Field of Classification Search
None
See application file for complete search history.

(56) References Cited

U.S. PATENT DOCUMENTS 5,269,777 A * 12/1993 Doiron ................... A61N 5/062
                                                         606/15
5,693,043 A * 12/1997 Kittrell .............. A61B 1/00096
                                                         606/15
(Continued)

*Primary Examiner* — Michelle R Connelly
(74) *Attorney, Agent, or Firm* — Bacon & Thomas, PLLC

(57) ABSTRACT

A distal end of an optical fiber may be protected by a variety of alternative protective caps, tips, and/or sleeves. In one example, a generally cylindrical soft tip is arranged to fit over the end of the fiber, and to compress in an axial direction when pressed against a stone to allow a recessed tip of the fiber to contact the stone or to be maintain a minimum spacing between the fiber tip and the stone and thereby limit erosion of the fiber tip.

19 Claims, 15 Drawing Sheets

(51) Int. Cl.
*A61B 18/00* (2006.01)
*A61B 1/00* (2006.01)

(56) References Cited

U.S. PATENT DOCUMENTS

| | | | | |
|---|---|---|---|---|
| 7,284,981 | B2* | 10/2007 | Schmid | A61B 1/24 |
| | | | | 362/109 |
| 7,775,969 | B2* | 8/2010 | Teichmann | A61B 1/018 |
| | | | | 600/106 |
| 8,864,754 | B2* | 10/2014 | Appling | A61B 90/94 |
| | | | | 606/15 |
| 9,907,616 | B1* | 3/2018 | Fried | G02B 6/24 |
| 2002/0183729 | A1* | 12/2002 | Farr | A61B 18/245 |
| | | | | 606/15 |
| 2009/0270907 | A1* | 10/2009 | Todd | A61B 17/221 |
| | | | | 606/198 |
| 2017/0079716 | A1* | 3/2017 | Zerfas | A61B 18/22 |
| 2019/0159839 | A1* | 5/2019 | Zhang | A61B 18/26 |

* cited by examiner

Tip compressed to make near or close contact

1 - buffered fiber

2 - stripped fiber

6 - laser fired to blow off cap

10 - cap w/ball tip

12 - hole formed in cap

50 - optical fiber
55 - soft tip
60 - buffer diameter
58 - fiber core
62 - soft tip stop
57 - n=index of refraction
65 - maximum fiber recess Example fiber dimensions 272 $\mu$m core
326 $\mu$m cladd
356 $\mu$m coat
420 $\mu$m buffer
0.22 Numerical Aperture
12.7° Half Angle $\theta$
1.0  n=index in air Fiber max recess TAN $\theta$ = $y/x$ = .23 x = maximum depth

Y = (420-272)/2 = 74 $\mu$m

X = Y/.23 = 321 $\mu$m

76 - buffer
74 - coating
72 - cladding
70 - core

Example fiber dimensions
---
272 μm core
326 μm cladd
356 μm coat
420 μm buffer
0.26 Numerical Aperture
15.07° Half Angle θ
1.0 n=index of air $\tan \theta = y/d = .27$ y = d = maximum depth $Y = (356-272)/2 = 42 \mu m$ $d = Y/.27 = 156 \mu m$   Air = n = 1

70 - core
72 - cladd
74 - coating
76 - buffer
80 - new buffer
85 - heat shrink
87 - flare to help
     placing onto fiber
89 - dopant $\lambda_1$ = Aiming beam
$\lambda_2$ = Excited phosphor 10 - Fiber tip (examples)

Cone

Orb

Flat

Angled

Angled coating (dielectric)

Metal w/angle

Angle with integral cap

Angle with protective tube

PROTECTIVE CAPS OF TIPS FOR SURGICAL LASER FIBERS

This application claims the benefit of provisional U.S. Patent Appl. Ser. Nos. 62/332,285, filed May 5, 2016; 62/336,888, filed May 16, 2016; 62/399,677, filed Sep. 26, 2016; and 62/465,407, filed Mar. 1, 2017, each of which is incorporated by reference herein.

BACKGROUND OF THE INVENTION

1. Field of the Invention

The invention relates to protective caps or tips that are placed over a surgical laser optical fiber to protect the working channel of an endoscope during insertion of the optical fiber through the endoscope in preparation for a treatment procedure.

The invention is especially applicable to the treatment procedure known as lithotripsy, in which laser energy is applied to a hard piece of material known as a stone, which can obstruct a patient's kidney or urinary tract. The laser radiation destroys or breaks up the stone so that it can pass more easily through and out of the patient's kidney, bladder, and/or ureter. The stone may be referred to herein by the terms "tissue," "tissue being treated," or "tissue to which radiation is applied," the term "tissue" being defined as "any of the distinct types of material of which animals or plants are made, consisting of specialized cells and their products," with kidney stones being one such product formed by a precipitate of minerals present in urine. While the invention is especially applicable to lithotripsy or stone removal procedures, the invention may also have application to surgical procedures involving targets other than kidney stones, and thus the term "tissue" is intended to cover any target of the surgical laser radiation, as well as, depending on context, surrounding tissues.

In a first preferred embodiment of the invention, a generally cylindrical soft tip is arranged to surround an end of the optical fiber to protect the working channel of the endoscope into which the fiber is inserted. In addition, the soft tip may be arranged to reduce erosion of the end face of the fiber during lasing, by extending beyond an end of the fiber and thereby maintaining a predetermined spacing between the end of the fiber and a stone or other tissue when the fiber end is extended from the scope. As a result, the soft tip provides an alternative to use of a ball-shaped or spherical fiber end to protect the scope, while at the same time reducing the need for re-cleaving of the fiber as a response to fiber erosion.

In addition to reducing the need for re-cleaving, the erosion protection provided by the soft tip allows the use of smaller fibers and/or higher treatment energies with, in the case of smaller lithotripsy fiber diameters, less stone retro-repulsion. The soft tip may also have the effect of enabling an operator to more easily determine when the fiber has been withdrawn into the scope, provide a warning when the fiber tip has been retracted beyond a bend in the scope, and/or eliminate saturation of the endoscope viewing screen caused by light flashes resulting from contact between the fiber tip and stone (or other target tissue) during treatment. Finally, by preventing or reducing the chance of contact between the fiber tip and the stone or tissue being treated, charring of the fiber caused by spikes in energy entering the fiber due to the light flashes can be eliminated.

In variations of the preferred embodiment, the soft tip may be made of a compressible material such as nylon, polyester, or Teflon™ that is fitted over a stripped section of the fiber core or cladding and held in place by welding or a compression fit. In one implementation, the soft tip is a section of fiber buffer that has been removed from another fiber.

According to alternative embodiments of the invention, instead of the multiple-use soft tips of the first preferred embodiment, single use tips may be provided to protect the scope during insertion of the fiber. The single-use protective caps or tips may, by way of example, be designed to (a) dissolve after insertion of the fiber through the endoscope; (b) be blown off the end of the fiber or ruptured by the shockwave or rapid heating and fluid expansion that occurs upon initial firing of the laser after insertion, (c) have a hole formed therein by vaporization of the portion of the protective cap that is in the path of the laser.

2. Description of Related Art

One problem with current optical fibers is that when the fibers are introduced into an endoscope, the fibers can score or puncture the soft working channel of the endoscope. The damage to the endoscope's working channel can be very expensive or even harmful to the patient.

A previously proposed solution to the problem of damage to the endoscope caused by sharp edges at the leading end of the fiber is to form a ball tip on the surface of the fiber tip. The ball tip eliminates the sharp edges, allowing the fiber to be passed through the endoscope even when the scope is deflected. However, this solution only provides protection during initial insertion of the fiber into the scope, before the fiber is used for lasing. Once the fiber is used, the exposed tip is quickly eroded and provides little to no protection for the working channel while repositioning the fiber into or out of the scope, as illustrated in the article entitled "*Comparison of Laser Fiber Passage in Ureteroscopic Maximum Deflection and their Influence on Deflection and Irrigation: Do We Really Need the 'Balltip Concept?'*", *World Journal of Urology*, DOI 10.1007/s00345-016-1873-8 (Jun. 14, 2016). In addition, the process of forming the ball tip necessitates removal of protective coatings on the fiber, and exposes the fiber to moisture during ball formation. The moisture causes static fatigue and weakens the fiber, leaving it subject to breakage inside the scope, as previously reported in the FDA MAUDE REPORTS.

Although a particular problem in the context of ball tips, conventional planar fiber end faces may also be subject to erosion. This phenomenon is described in the article "*Hollow steel tips for reducing distal fiber burn-back during thulium fiber laser lithotripsy*" in the *Journal of Biomedical Optics*, 18(7), 078001, SPIE (July 2013), which proposes a solution to fiber end face erosion that involves permanently affixing a hollow steel tip to the end of the fiber. An example of a similar hollow metal tip is disclosed in U.S. Patent Publication No. 2008/0188843. However, while the hollow metal tip serves as a spacer to prevent the fiber tip from touching a stone, thereby reducing erosion, the metal tip only exacerbates the problem of damage to the working channel of the scope, since the metal tip will increase the risk of scoring or puncturing the working channel, Furthermore, the use of a hard or metal tip can increase the risk of damaging delicate tissue surfaces such as the mucosa found in the ureter, either by physically damaging the tissue surfaces or by excessive heat due to absorption of treatment radiation by the metal tip.

Another possible solution to the problems of fiber tip erosion and protection of the scope's working channel is to remove a worn or jagged fiber tip by simply cutting off the worn fiber tip, for example by using scissors. However, scissors or other blades can still leave jagged edges that can damage the endoscope or introducer into which the fiber is inserted, and furthermore leaves the fiber vulnerable to peeling of the buffer, as illustrated in FIGS. 8A to 8C, in which an eroded fiber 41 having a buffer 42 and cladding 48 is cut with scissors along a cut line 49 to obtain a freshly cut fiber 47 (FIG. 8B), but nevertheless is vulnerable to erosion and buffer peeling after lasing, as shown in FIG. 8C.

By way of background, it is known to completely enclose a fiber tip within a quartz ferrule that is permanently secured to the tip of the fiber, as disclosed for example in the inventor's U.S. Pat. No. 9,345,543. Such ferrules are used in applications such as endovascular surgery to prevent a radially-firing fiber tip from contacting a vein. However, they are not suitable for urological or other applications that involve end firing lasers subject to erosion of the fiber end-face.

In the context of end-firing fibers used in urological and similar applications, neither spherical ball tips nor hollow steel tips nor re-cleaving of the fiber tip during or between treatment procedures has proven effective in solving the problems of scope damage and fiber end-face erosion to which such fibers are subject. To the contrary, fiber tip erosion continues to be a serious problem, with effects that cannot be eliminated by spherical ball tips, hollow steel tips, or even frequent re-cleaving of the fiber tip during a treatment procedure. These effects include limitations on treatment energy and fiber diameter, which in turn result in prolonged treatment time and enhanced retro-repulsion between the laser and the stone or other object or tissue being targeted by the laser.

Still further, the use of unprotected fiber tips has led to previously unappreciated or unaddressed problems resulting from flashes that occur upon contact between the fiber tip and stones or other tissues. One such problem is the problem of saturation of the endoscope camera as a result of the flash-induced influx of light energy, which can temporarily cause the loss of vision of the treatment site. However, an even more potentially serious problem is the problem of charring caused by the energy influx, which can create weaknesses in the fiber at points located a significant distance away from the fiber tip.

The charring occurs as a result of thermal absorption of the energy influx in fibers have a colored buffer to enhance fiber visibility in a fluid environment or in the operating room. In such fibers, the tip is conventionally left undyed, but at least a portion of the fiber upstream of the tip is dyed either blue or green. When a flash occurs, a white flash enters the fiber and is absorbed by the dyed portion of the buffer, whereupon charring can occur within seconds, causing a weak spot in the buffer that is not easily visible through the scope but that can lead to sudden and unexpected fiber breakage.

The charring effect, like the saturation effect, can be alleviated by preventing contact between the fiber tip and the tissue being treated, but such contact prevention using a bare fiber tip is difficult or impossible to achieve in practice, or is contrary to common surgical techniques. For example, in stone lithotripsy, it is common for a surgeon to pin the stone against surrounding tissue with the bare fiber tip to keep it from moving.

SUMMARY OF THE INVENTION

It is accordingly an objective of the invention to provide a cost-effective way to protect an endoscope from damage caused by insertion of the fiber or fiber assembly into the endoscope, which does not interfere with fiber performance.

It is a further objective of the invention to provide a cost-effective way to limit fiber tip erosion and at the same time protect an endoscope from damage caused by insertion of the fiber or fiber assembly into the endoscope.

It is a still further objective of the invention to minimize scope damage from fiber pull-in during lasing.

It is another objective of the invention to eliminate or minimize overheating of the fiber tip upon contact between the fiber tip and a stone or other tissue, which may lead to a bright "fuse" or "white out" effect that creates undesired camera image effects during lasing, and/or which may lead to charring and potential breakage of the fiber as a result of thermal absorption of the flash radiation by a material of the buffer.

It is another objective of the invention to allow a fiber to pass into a scope without scope damage, even when the scope is fully deflected.

It is another objective of the invention to provide a position indicator that continues to provide a useable indication of fiber tip position throughout a treatment procedure, or even multiple procedures, because of the reduced erosion and need for re-cleaving that would otherwise alter the relative positions of the position indicator and fiber tip.

In a first preferred embodiment of the invention, protection of the working channel of the scope and/or prevention of fiber end-face erosion is provided by a protective sleeve structure in the form of a soft tip having a generally cylindrical exterior surface and a central bore arranged to be fitted over the stripped core or cladding of the fiber and to remain there during at least one treatment procedure.

In the first preferred embodiment, the protective sleeve structure is preferably made of a soft or resilient material that prevents damage to the scope or introducer into which the fiber is inserted, and that permits the sleeve structure to compress in an axial direction and thereby enable the fiber tip, which is initially recessed from an end of the sleeve structure, to touch or maintain a minimum spacing from a stone against which the end of the sleeve structure is pressed. Instead of a shoulder, the sleeve structure may contain a separate structure for defining the set back of the fiber tip within the sleeve structure.

In addition, the outside diameter of the protective sleeve structure of the first preferred embodiment is preferably either sufficiently narrow to enable fluid within the scope or introducer to flow past the sleeve structure, or the sleeve is short enough that the entire sleeve extends out of the scope, and therefore does not impede fluid flow, during lasing.

A suitable soft or resilient material of the first preferred embodiment is the material of the fiber buffer. One way to prepare such a protective tip is to remove cylindrical sections of buffer material from an optical fiber provided for that purpose, and to place one of the protective tips placed over a stripped end of an optical fiber to be used in a treatment procedure. A section of buffer material may also be cut from the treatment fiber, and slid axially so that it extends beyond the tip of the treatment fiber, with the resulting gap being filled-in with an adhesive material or bridged by an adhesive or heat shrink sleeve.

The soft tip of this embodiment may also be made of a soft plastic material such as polytetrafluoroethylene (Teflon®) or ethylene tetrafluoroethylene (ETFE) and welded, glued, or compression fit to an outer diameter of a fiber buffer or coating so that it does not cause significant interference with water flow or scope deflection. The material is preferably selected so that absorption of therapeutic laser energy is minimal. Transparent fiber materials are generally less absorptive to the laser energy, and in addition have the advantage of being distinguishable from the fiber buffer, which is typically colored to improve visibility. The length of the soft tip may be on the order of 5-10 mm, while the thickness should be sufficient to handle shock waves created by the laser pulses.

The soft tip may have a cylindrical central bore or an increased-diameter or stepped section arranged so that the tip can be fitted over both a stripped section of the fiber and a section of the fiber that still has the fiber buffer. The shoulder between the respective narrower and wider diameter sections of the central bore defines a length of the narrower diameter section, so that the tip of the fiber is initially set back from the end of the sleeve structure when the distal end of the buffer engages the shoulder.

The protective tip may further be provided with a dopant that emits light when excited by the therapeutic laser source or the aiming beam. The emission could aid the surgeon in locating the soft tip should it break off the fiber.

Finally, with respect to the soft tip embodiment, the protective tip may take the form of a soft sleeve that is arranged to be fitted over an already eroded fiber and which serves to prevent peeling of the buffer after cutting of the fiber to remove the eroded tip. The soft sleeve also prevents the fiber tip from contacting the scope to prevent damage to the scope during pullback or insertion following further erosion of the cut end of the fiber, which may result from contact with a stone or tissue being treated.

By limiting erosion and preventing contact between the fiber tip and a stone or tissue being treated, the soft tip of the preferred embodiment reduces treatment time and expense, and can even facilitate such common procedures as using the fiber tip, now protected by the soft tip of the preferred embodiment, to pin a stone against surrounding tissues in order to keep the stone from moving.

Alternatively, at least the first objective of the invention may be achieved by providing a single-use cap that can be fitted over the end of the fiber before insertion into the endoscope or other introducer. The cap is made of a non-toxic material that has sufficient resiliency or adhesion properties to remain on the fiber during insertion, but that is designed to be removed from the fiber as a result of air, vapor or fluid expansion upon initial firing of the laser during a treatment procedure. Alternatively, the cap may be designed to remain on the fiber through the treatment procedure, but to have a hole formed therein upon initial firing of the laser by vaporization or as a result of physical destruction due to fluid expansion, so that the cap does not interfere with the treatment procedure.

For applications where the cap, or a portion of the cap, remains in the patient after treatment, the material of cap may be selected to be dissolvable in water or an aqueous solution, so that it will eventually dissolve within the patient's body. If the cap is designed to have a hole formed therein upon initial firing of the laser, but to remain on and be removed with the fiber after treatment, the cap may optionally be made of a non-dissolvable material.

The material must be capable of being formed or shaped to prevent scoring of the working channel of the introducer during insertion of the fiber. However, the shape is not limited to a spherical shape, but rather may be have any of a variety of shapes, including curved shapes that enable the protective cap or tip to also serve as a guide for insertion of the fiber into an organ such as a kidney.

Suitable nontoxic dissolvable materials are readily available and include those commonly used in medicine capsules or gel caps, such as gelatin from bovine or vegetable sources, such as pullulan, or hypromellose.

DETAILED DESCRIPTION OF THE PREFERRED EMBODIMENTS

Figure 1:
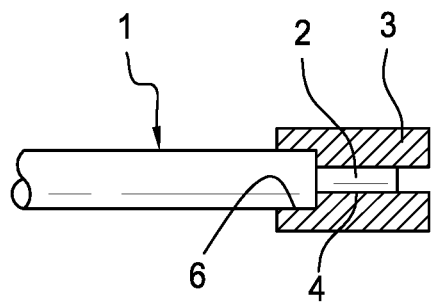
FIG. 1 is a cross-sectional side view of an optical fiber soft tip or sleeve structure arranged in accordance with principles of a first preferred embodiment of the invention.
Figure 2:
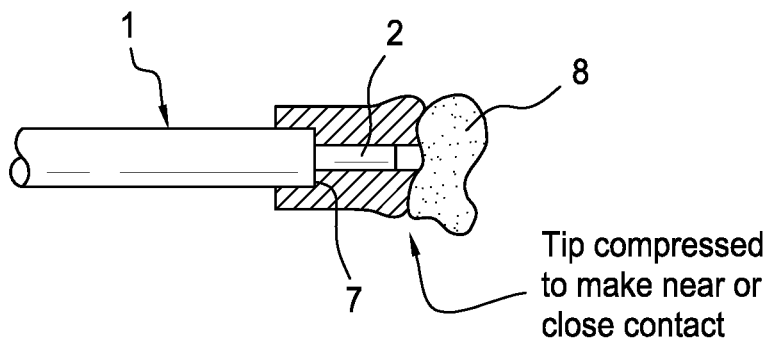
FIG. 2 is a cross-sectional side view illustrating the manner in which the soft tip or sleeve structure of FIG. 1 compresses against a stone during a treatment procedure.
Figure 3:
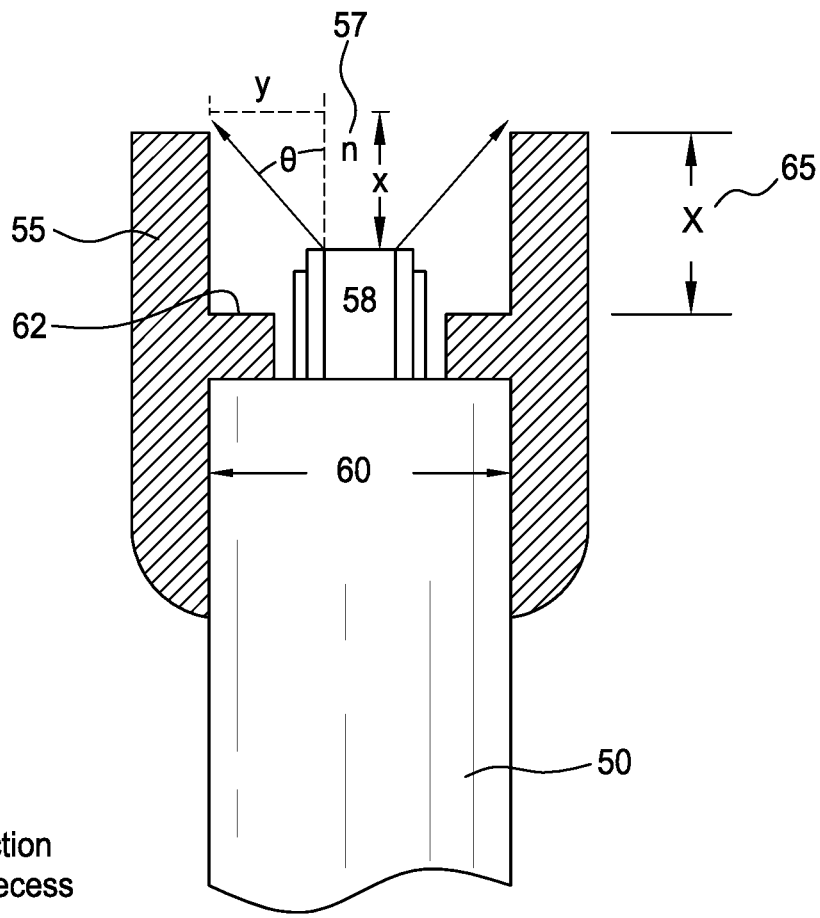
FIG. 3 shows details, including various dimensions, of the embodiment illustrated in FIGS. 1 and 2.

As shown in FIGS. 1-3, the distal end of an optical fiber 1 used in laser surgery applications is surrounded by a soft tip or protective sleeve structure 3 (hereinafter referred to as a "soft tip") that protects an endoscope from damage as the optical fiber is inserted into the scope prior to lasing, and that also reduces erosion of the end face of the fiber during lasing. The fiber 1 is, by way of example, an end-firing fiber of the type used in urological stone removal applications, although the soft tip or protective sleeve structure of this embodiment of the invention is not necessarily limited to stone removal or urological applications, or to end-firing lasers, but rather may be used in connection with any optical fiber through which radiation or laser energy is supplied to tissues or other objects in the treatment area that may come into contact with an end section or face of the fiber.

The soft tip 3 has a generally cylindrical exterior surface and a central bore. The fiber 1 over which the soft tip 3 is positioned may have an end section that is stripped of its buffer and, optionally, some or all of the cladding, leaving a section 2 made up of the bare core or a core and at least a portion of the fiber cladding. If the fiber end is stripped, then the soft tip may include both a narrow diameter section 4 arranged to at least fit over the stripped core or cladding 2 of the fiber, and an increased diameter section 6 arranged to fit over the fiber buffer 1. In that case, the shoulder 7 between the respective narrower and wider diameter sections 2, 6 of the central bore defines a length of the narrower diameter section, the tip of the fiber being set back from the end of the sleeve structure when the distal end of the buffer engages the shoulder 7.

Instead of the shoulder 7 shown in FIGS. 1 and 2, a modified soft tip 55 for protecting fiber 50 having a buffer whose diameter is indicated by reference numeral 60 and a stripped core/cladding section 58 may include a separate, inwardly-extending, annular collar or flange 62 for defining the set back of the fiber end face within the soft tip, as shown in FIG. 3. Also shown in FIG. 3 are calculations illustrating the manner in which the maximum fiber tip set-back x may be selected, based on the numerical aperture of the fiber, to achieve a desired emission angle at which a laser beam used in urological procedures will exit the fiber. For example, for a fiber with a core diameter of 272 µM, cladding outer diameter of 326 µM, coating outer diameter of 356 µM, buffer outer diameter of 420 µM, numerical aperture of 0.22, a radiation emission half angle of 12.7° can be achieved by choosing the set-back x to be 321 µM.

The soft tip 3 shown in FIGS. 1 and 2 or the soft tip 55 shown in FIG. 3 are preferably made of a soft or resilient material, such as nylon, polyester, or Teflon™, that prevents damage to the scope or introducer into which the fiber is inserted and that permits the soft tip 3 to compress in an axial direction, as shown in FIG. 2, and thereby enable the end face of the fiber 1, which is initially recessed from an end of the soft tip 3, to touch or move to a position that is spaced by a predetermined distance from the stone during a treatment procedure.

In a variation of the soft tips of FIGS. 1-3, the soft tip may have a uniform diameter bore, without any shoulder or set back defining structure. Also, in each variation, the front or rear body of the soft tip may optionally be rounded to ease insertion and withdraw of the fiber inside the endoscope, and have an outer diameter that is sufficiently narrow to enable fluid within the scope or introducer to flow past the sleeve structure.

Figure 4A:
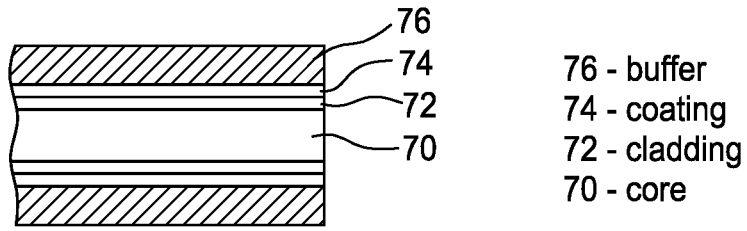
FIG. 4A shows a conventional treatment fiber which is to be stripped and provided with a protective soft tip or sleeve structure made of a same material as a buffer of the fiber.
Figure 4B:
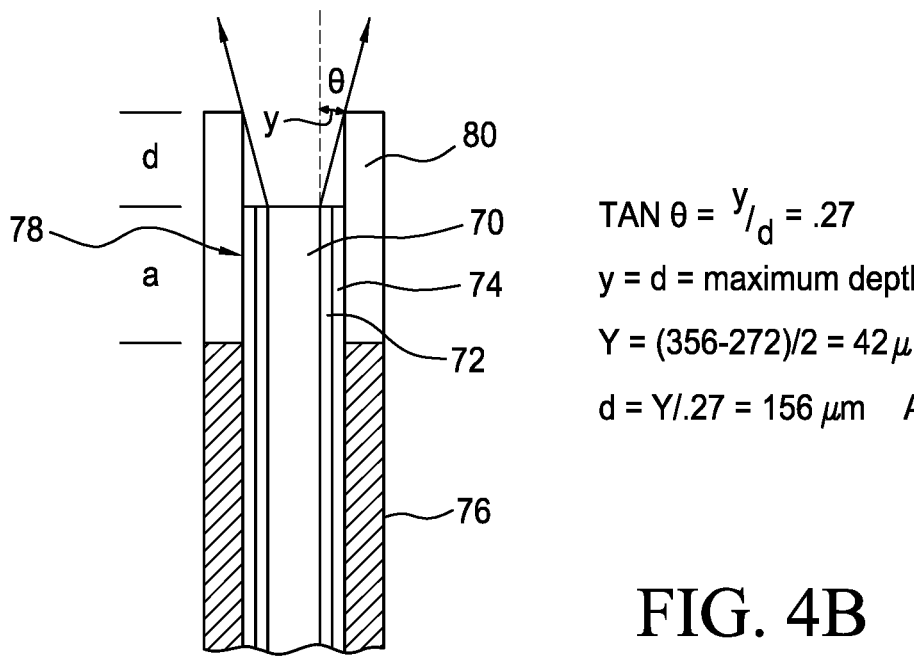
FIG. 4B shows a variation of the embodiment of FIGS. 1-3, in which a fiber of the type illustrated in FIG. 4A is provided with a protective soft tip or sleeve structure in the form of a cylindrical section of buffer material.

FIG. 4B illustrates a variation of the soft tips of FIGS. 1-3, in which a soft tip 80 is formed of a buffer material. A conventional treatment fiber having a buffer 76, coating 74, cladding 72, and core 70, as illustrated in FIG. 4A, is stripped of its buffer layer to a distance a from the tip of the fiber. The stripped buffer material is replaced by a cylindrical buffer section 80 having a length a+d. The added buffer section 80 may, for example, be stripped from another optical fiber (not shown). Because the added buffer section 80 has a length a+d and the stripped portion 78 of the optical fiber to which the buffer section 80 is added has a length d, the buffer section 80 will extend by a distance d beyond the tip of the fiber, and therefore provide erosion protection similar to that provided by the sleeve structure of the FIGS. 1-3.

Figure 5A:
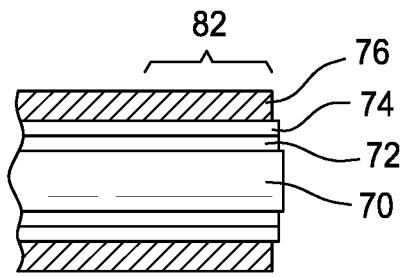
FIGS. 5A-5D illustrate a method of assembling the protective soft tip or sleeve structure of FIG. 4B to an optical fiber of the type illustrated in FIG. 4A.
Figure 5B:
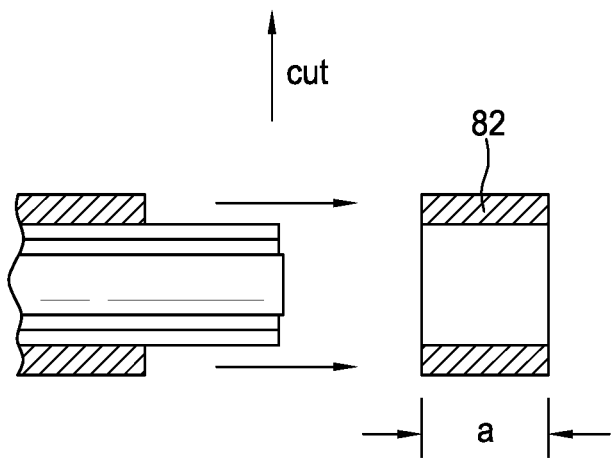
Figure 5C:
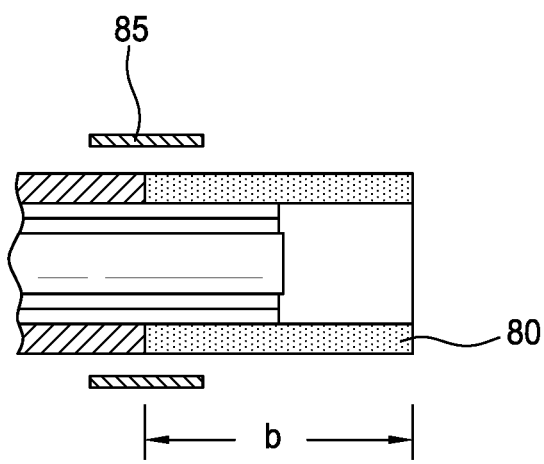
Figure 5D:
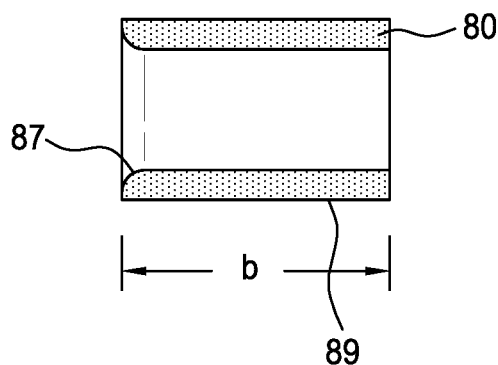

One method of making forming the protective soft tip 80 of FIG. 4B is illustrated in FIGS. 5A-5D. As illustrated in FIG. 5A, when it is desired to add a new protective soft tip, the original buffer material of an optical fiber such as the optical fiber of FIG. 4A is initially cut to define a buffer section 82 of length a, and the section 82 is removed or stripped from the fiber, and removed, as illustrated in FIG. 5B. A new section of buffer material, which forms protective soft tip 80 having length b=a+d (see FIG. 4B) is fitted over the stripped end of the fiber and secured in place, so that the fiber of the fiber has a setback of length d=b−a, as illustrated in FIG. 5C. The protective tip made up of the new extended-length section of buffer material that forms protective soft tip 80 may be secured in place in a variety of ways, including by an adhesive sleeve or tape, or a heat shrink sleeve 85 as illustrated in FIG. 5C. In a variation shown in FIG. 5D, the replacement soft tip 80 may be flared to facilitate placement of the fiber tip into the cylindrical buffer section 78.

Although the protective soft tip 80 may be in the form of a replacement buffer section that is made of the exact same material as the removed buffer material 82, it is possible to alter the material of the soft tip without affecting its compressibility or protective properties. For example, a dopant may be added that emits light when excited by the therapeutic laser or aiming beam or other light source. Such emission could be useful to the surgeon in locating the tip if it were to become dislodged from the fiber. Also, while the illustrated soft tip 80 has a thickness that corresponds to that of the original buffer material, so that the tip does not interfere with passage of the fiber through the introducer or with the flow of irrigation fluid, the soft tip may alternatively be arranged to have a greater thickness to help keep the fiber tip from contacting the scope's working channel.

Figure 6A:
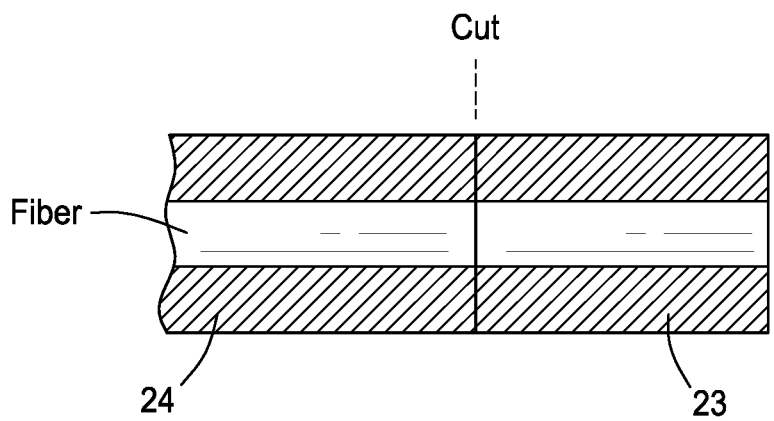
FIGS. 6A to 6D illustrate an alternative method for providing a protective soft tip sleeve structure that is made up of a section of buffer from optical fiber to be protected.
Figure 6B:
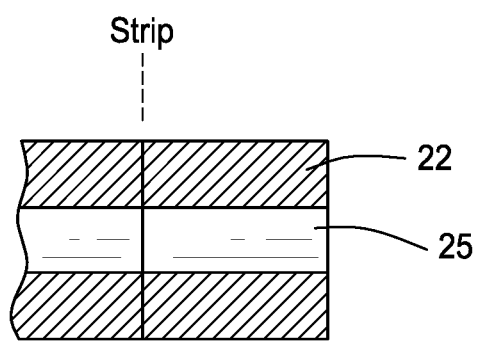
Figure 6C:
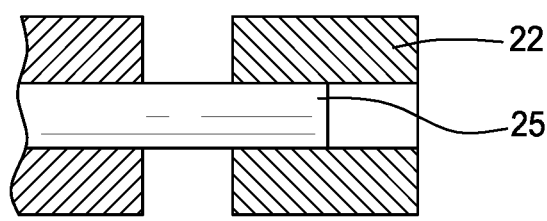
Figure 6D:
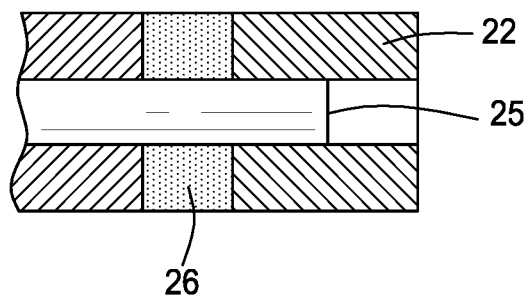

As shown in FIGS. 6A to 6D, instead of separately forming or providing a protective soft tip, the soft tip may be formed by cutting a buffer section 22 from the optical fiber 23 to be protected, rather than from a different optical fiber as in the method illustrated in FIGS. 5A to 5D. For example, after cutting the fiber 23 in order to remove an eroded tip, as shown in FIG. 6A, the remaining portion 24 of the fiber may be cut by a wire stripper or similar tool of appropriate diameter in order to free the buffer section 22, as illustrated in FIG. 6B. The fiber section 22 may then be axially moved by a distance d away from its original position, as illustrated in FIG. 6C so that the fiber section 22 extends beyond the tip 25 of the fiber and the tip 25 is recessed by the distance d, thereby forming a protective soft tip from the material of the fiber itself. The resulting gap 26 may be filled in by an adhesive material to maintain the desired spacing, as illustrated in FIG. 6D.

Figure 7A:
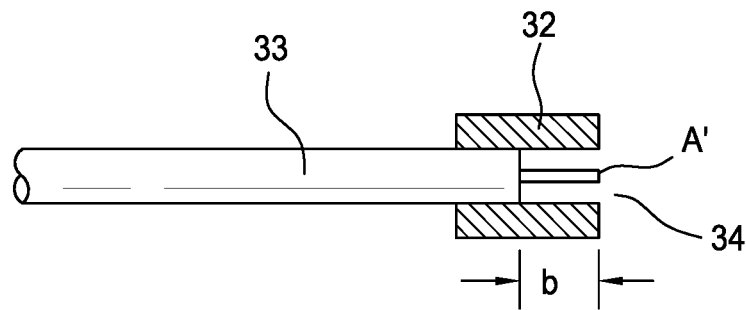
FIGS. 7A to 7D show further variations of the protective soft tips or sleeve structures of the first preferred embodiment of the invention.

In the soft tip variation illustrated in FIG. 7A, a protective soft tip 32 is in the form of a cylindrical structure made of a soft plastic material such as polytetrafluoroethylene (Teflon®) or ethylene tetrafluoroethylene (ETFE) and welded, glued, or otherwise attached to an outer diameter of a fiber buffer or coating 33, rather than being cut out of or replacing a section of buffer. In this embodiment, the soft tip 32 extends a distance A sufficient to surround a stripped portion 34 of the fiber. Preferably, the outer diameter of the soft tip 32 is thin enough that the soft protective tip does not cause significant interference with water flow or scope deflection, while still being sufficient to handle shock waves created by the laser pulses. The length of the soft tip 32 may be on the order of 5-10 mm in which case, if sufficiently rigid, the presence of soft protective tip 32 will typically limit fiber erosion to 100-200 µm. On the other hand, additional initial erosion protection may be provided by pre-cleaving the fiber by a length R so that the fiber tip A is recessed or set back from the leading edge of the soft protective tip 32.

In any of the variations where the protective soft tip is made of a material other than the material of the fiber buffer, the material of the soft tip 32 is preferably selected so that absorption of therapeutic laser energy is minimal. For example, the protective soft tip may optionally be made of a transparent material since transparent fiber materials are generally less absorptive to the laser energy, and in addition have the advantage of being distinguishable from the fiber buffer, which is typically colored to improve visibility. In some cases, having the buffer clear allows the surgeon to verify optically the position of the fiber within the soft tip.

Those skilled in the art will appreciate that the fiber tip need not be flat when used with the soft protective tip 32, as illustrated, by may also be faceted, ball-shaped, conical, or have other shapes.

Figure 7B:
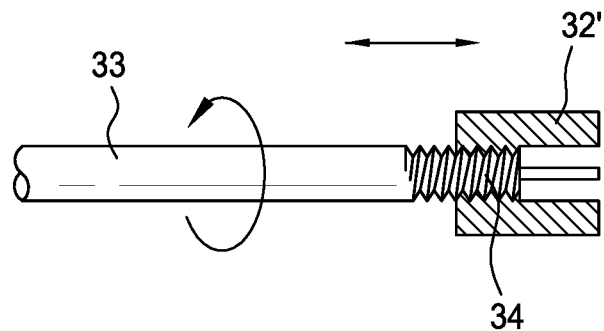

In a modification of the embodiment shown in FIG. 7A, shown in FIG. 7B, a soft protective tip 32' may be attached to the fiber buffer or coating 33 by threading the protective tip onto an externally threaded end section 34 of the buffer or coating. This option has the advantage that the soft fiber tip can be readily replaced, and also that the position of the fiber tip relative to the leading edge of the protective tip 32' can be adjusted by rotating the tip, which will cause the tip to move axially.

Figure 7C:
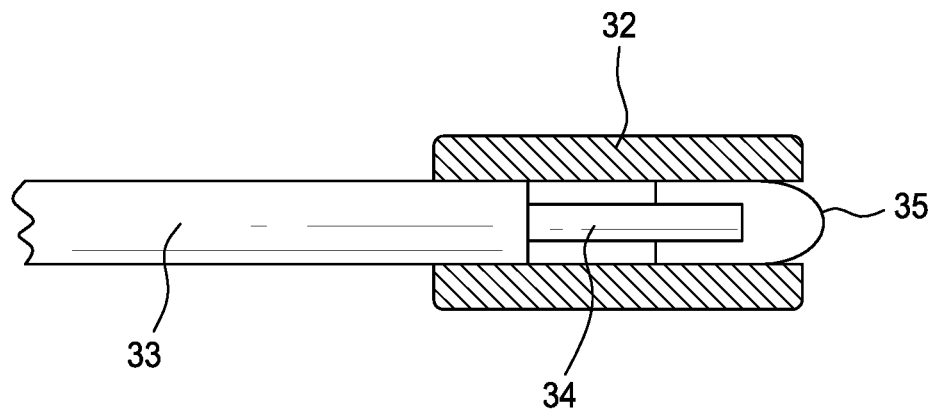

In yet another modification of the embodiment shown in FIG. 7A, shown in FIG. 7C, further protection for the fiber tip is provided by the addition of a plug 35 made of PTFE or a similar material soft enough to prevent mechanical damage to the scope or non-target tissues.

Figure 7D:
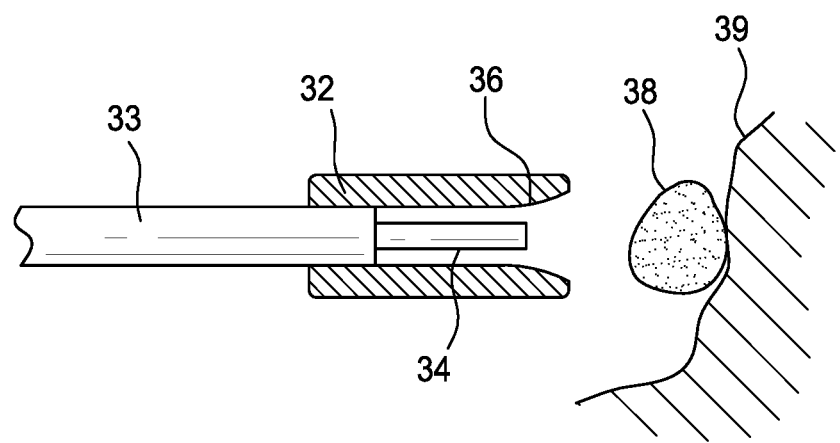
Figure 7D:
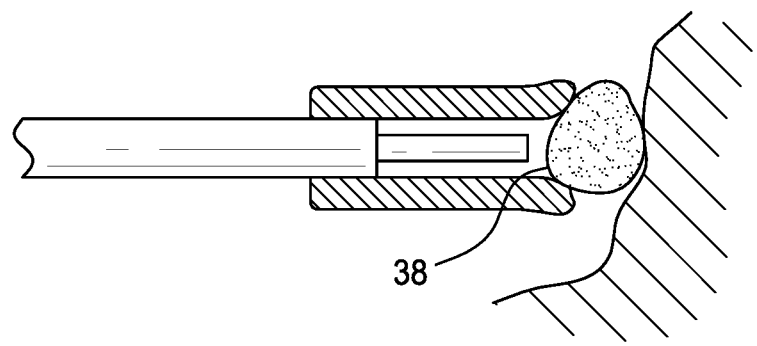

FIG. 7D illustrates a modification of the soft tip of FIG. 7A, which is designed to facilitate the surgical technique of using the fiber tip to pin a stone 38 against other tissues 39, so as to keep the stone from moving during a lithotripsy procedure. The modification is to increase the flexibility of the end of the soft tip by, for example, beveling or reducing the thickness of the tip, so as to enable the tip to, in effect, grasp or tightly fit around the stone, and thereby secure the stone while maintaining a desired separation distance between the actual tip 34 of the fiber and the stone 38 to avoid erosion and charring.

Figure 10A:
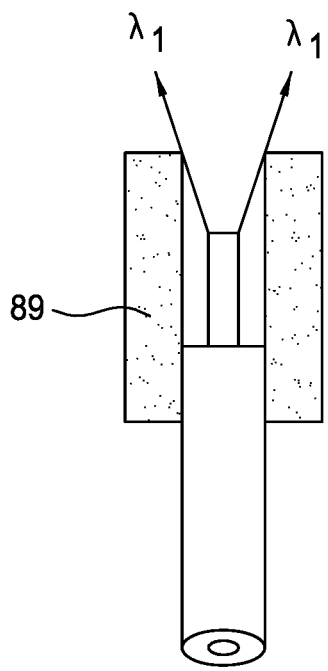
FIGS. 10A to 10C show an implementation of the first preferred embodiment described in connection with FIGS. 1 to 9D, in which a protective soft tip or sleeve structure is doped with a phosphor that emits light when the fiber tip erodes too far into the soft tip, causing an aiming beam to excite the phosphor.
Figure 10B:
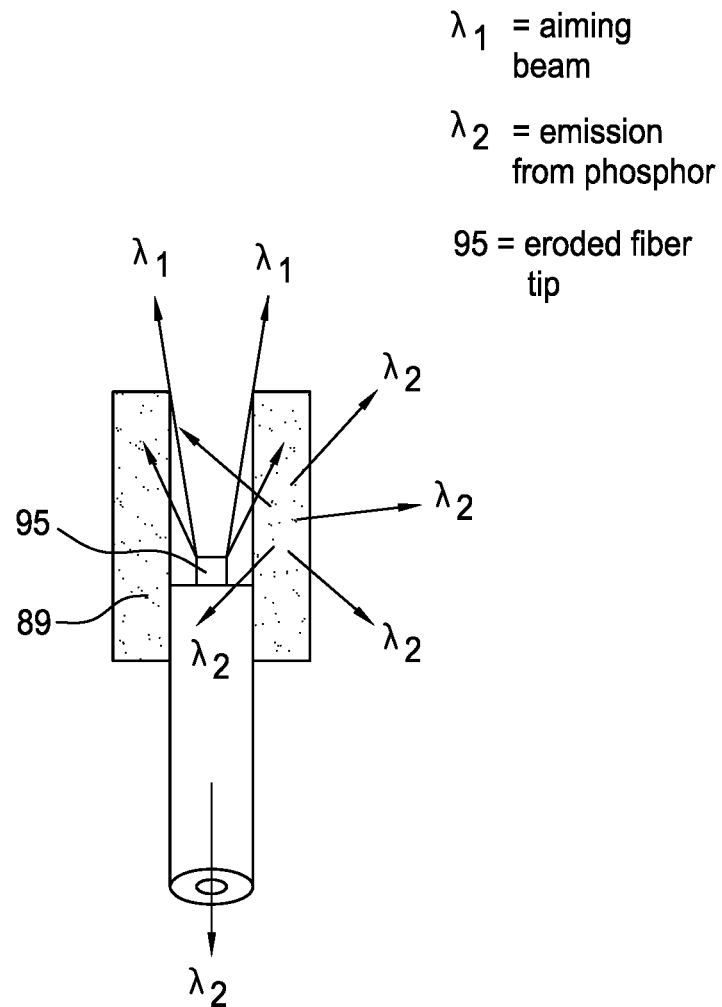
Figure 10C:
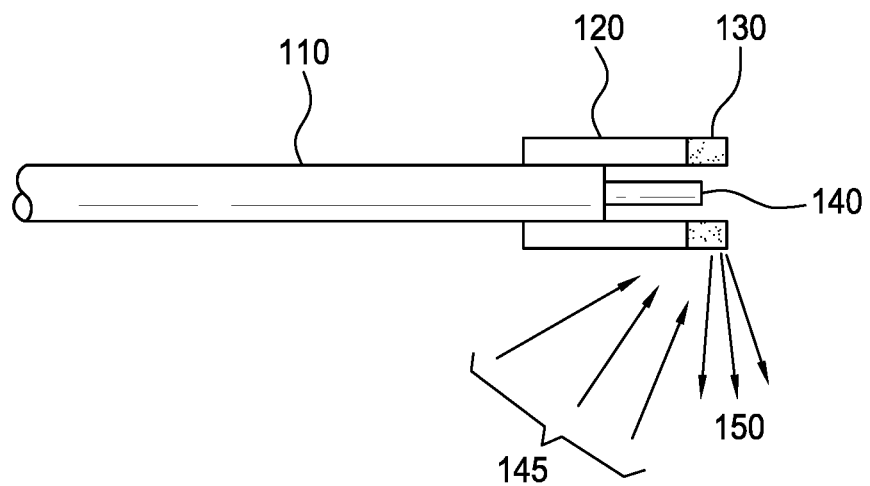
Figure 10D:
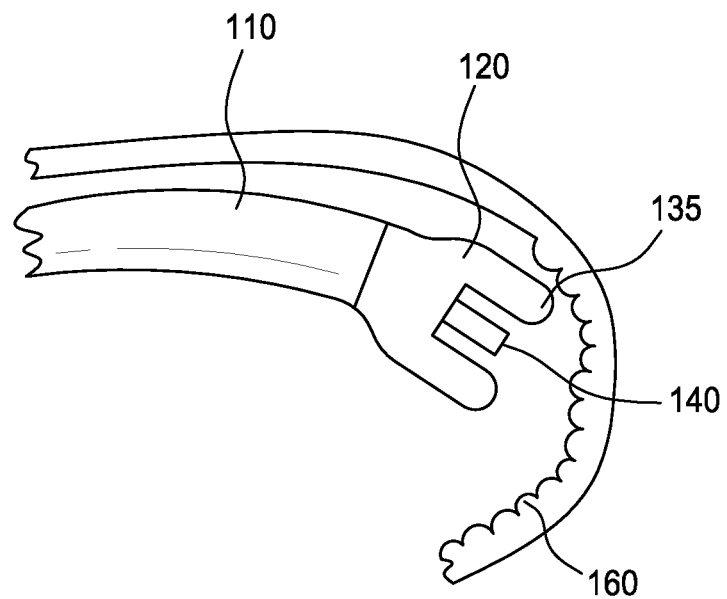
FIG. 10D shows a variation of the soft tip illustrated in FIG. 10C, in which the protective soft tip further has a rounded leading edge.

As with the variations of the first preferred embodiment discussed above, those skilled in the art will appreciate that the soft protective tips 32, 32', and/or plug 35, shown in FIGS. 7A-7C may be doped with phosphors that emit radiation when laser energy is incident on the inner diameter of the soft protective tip. Such emission would indicate that the tip of the fiber has eroded and needs to be replaced. An example of a doped soft tip is illustrated in FIGS. 10A and 10B. When the fiber tip 95 erodes too far into the soft tip, then the aiming beam will be deflected by the eroded surfaces to be incident on and excite phosphors 89 in the soft tip, resulting in emissions by the phosphors that can be detected at the proximal end of the fiber to provide an indication of the erosion. Alternatively, as shown in FIG. 10C, the distal end 130 of a soft tip 120 at the end of fiber 110 may be doped to emit light when illuminated by light from the aiming beam, or light 145 of any wavelength that is present in the scope, so as to indicate the location of the fiber tip 40. If light other than the aiming beam is used to excite the phosphors, the phosphor emissions can be used to locate the fiber tip even when the aiming beam has been turned off in the event that forward illumination from the fiber tip is blinding the image of the target stone or tissue. As illustrated in FIG. 10D, the distal end 135 of the soft tip of this variation of the preferred embodiment, whether provided with phosphors or not, may be further rounded or founded into a spherical or partially spherical shape to protect the working channel of the scope, and to facilitate passage through the working channel in case the working channel has bump, prior score damage, ridges, or other obstacles that can collide with a non-rounded tip and impede passage. It will be appreciated that, even though the soft tip prevents erosion in a fiber with a planar tip, it is also possible to use the soft tip with fibers having a rounded or ball tip.

Figure 8A:
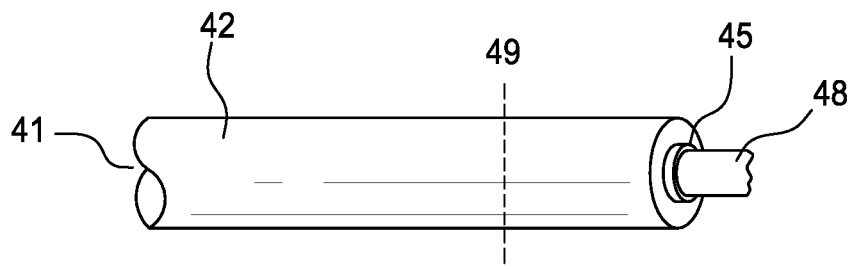
FIGS. 8A to 8C show effects of cutting or cleaving an eroded fiber.
Figure 8B:
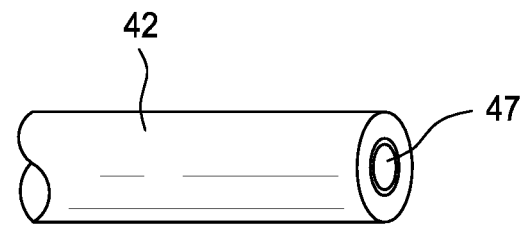
Figure 8C:
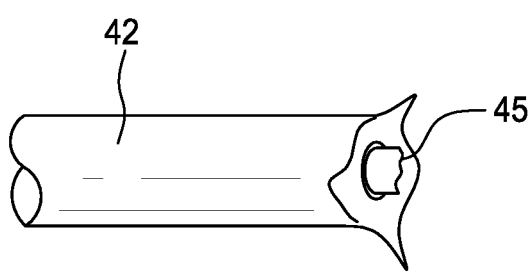
Figure 9A:
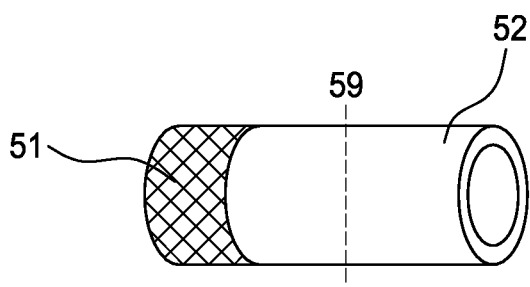
FIG. 9A shows a further variation of the protective soft tip or sleeve structure of the first preferred embodiment, in which the protective soft tip or sleeve structure is fitted over an eroded fiber and cut along with the eroded fiber.

FIGS. 9A to 9D show yet another variation of the first preferred embodiment of the invention, which is designed to protect a scope and address the fiber erosion and peeling problem illustrated in FIGS. 8A to 8C. FIG. 9A shows a cylindrical sleeve 52 made of a relative soft material, such as the material of the fiber buffer 53 or a material such as PTFE or ETFE. The sleeve 52 includes a cut line 59, and a visual indicator 51 made up of colored markings or a band of colored material to enable a clinician to more easily observe the location of the fiber tip, despite the sleeve being made of a transparent material to avoid absorption of errant laser radiation.

Figure 9B:
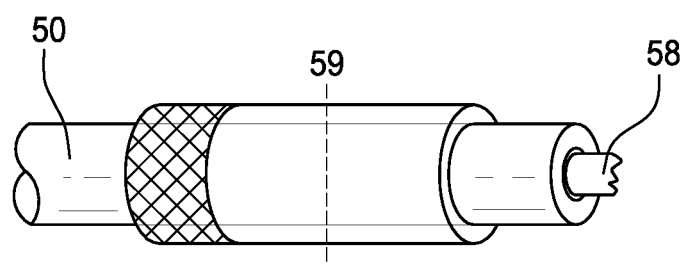
FIGS. 9B and 9C are respective views of the protective soft tip or sleeve structure of FIG. 9A installed on an eroded fiber, taken before and after cutting.
Figure 9C:
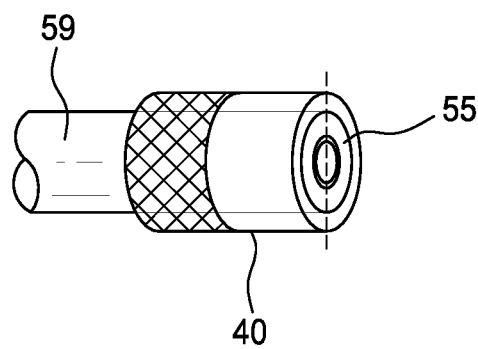
Figure 9D:
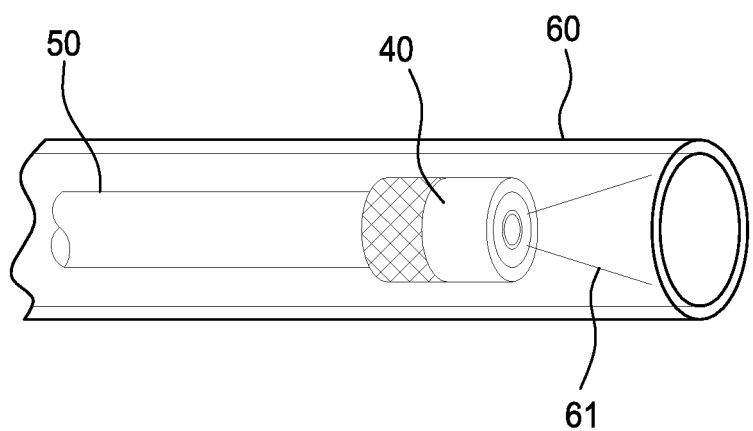
FIG. 9D illustrates the relationship the cut soft sleeve arrangement of FIG. 9C, after unintentional pullback of the fiber and sleeve into the working channel of an endoscope.

As illustrated in FIG. 9B, the soft sleeve 52 is placed over the fiber 50 such that an end section 56 with an eroded tip 58 protrudes from the sleeve 52. The sleeve 52 and fiber 50 are then cut at the cut line 59 to create a new, freshly cut soft tip 40. The core/cladding tip 55 will still erode upon contact with a stone or tissue during lasing, until the eroded tip is set back and no longer able to contact the stone, automatically reducing further erosion while any sharp or jagged edges of the tip are kept safely within the sleeve 52, and therefore will not score or puncture the working channel of a scope. In addition, the larger outer diameter of the soft sleeve 52 provides added separation between the fiber and the inner diameter of the working channel a scope 60 in case of accidental pullback while lasing, as illustrated in FIG. 9D, lowering the power density of the laser 61 that is incident on the scope as a result of the pullback. If more compression is required, a crimp ring can be added before cutting.

Figure 11A:
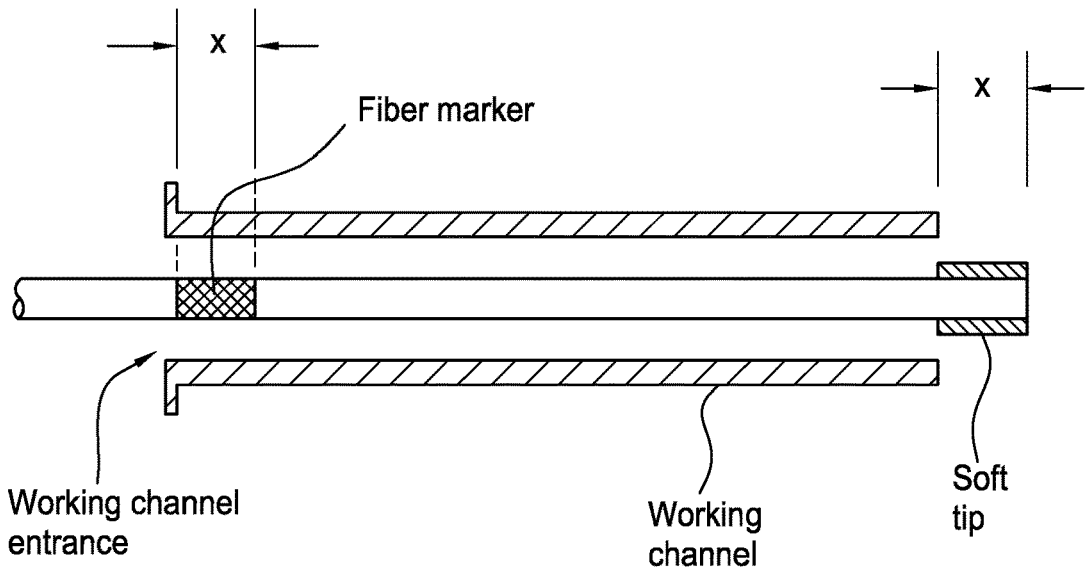
FIGS. 11A and 11B illustrate the manner in which use of a protective soft tip or sleeve structure of the first preferred embodiment described in connection with FIGS. 1 to 9D facilitates use of markers to provide warning of excessive pull back or tip location.
Figure 11B:
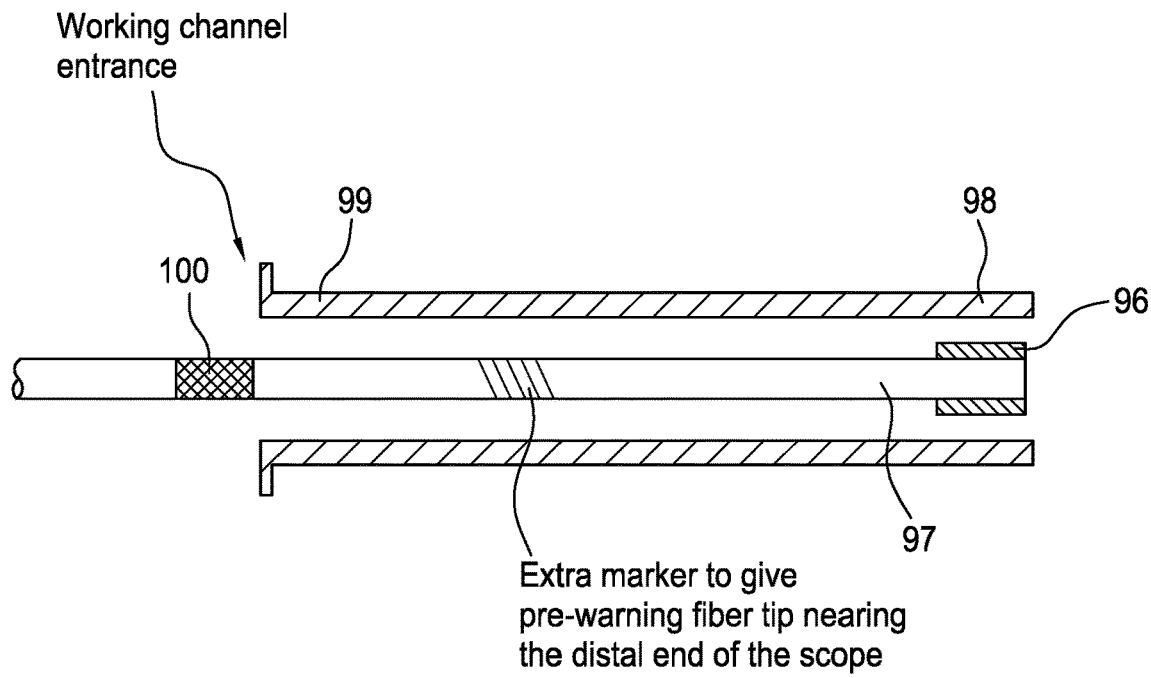

In the preferred embodiment and variations thereof illustrated in FIGS. 1-10, the inclusion of the soft tip eliminates or substantially reduces the need to re-cleave the fiber before each procedure, or multiple times during a procedure. As a result, as illustrated in FIGS. 11A and 11b, it is possible to provide markers to provide an added warning that the distal end of the fiber 97 has been pulled back into the distal end 98 of the scope, as shown in FIGS. 11A and 11B. The reason is that, since the presence of the soft tip 96 eliminates the need to repeatedly re-cleave and thereby shorten the fiber 97, a marker at the proximal end 99 of the scope will provide an accurate indication of the location of the distal end of the fiber, and therefore observation of an appropriately placed proximal marker 100 at the entrance to the scope will also indicate the withdrawal of the distal end of the fiber into the distal end of the scope. Additional markers 91 may be added to provide pre-warning of excessive pull back.

Figure 12A:
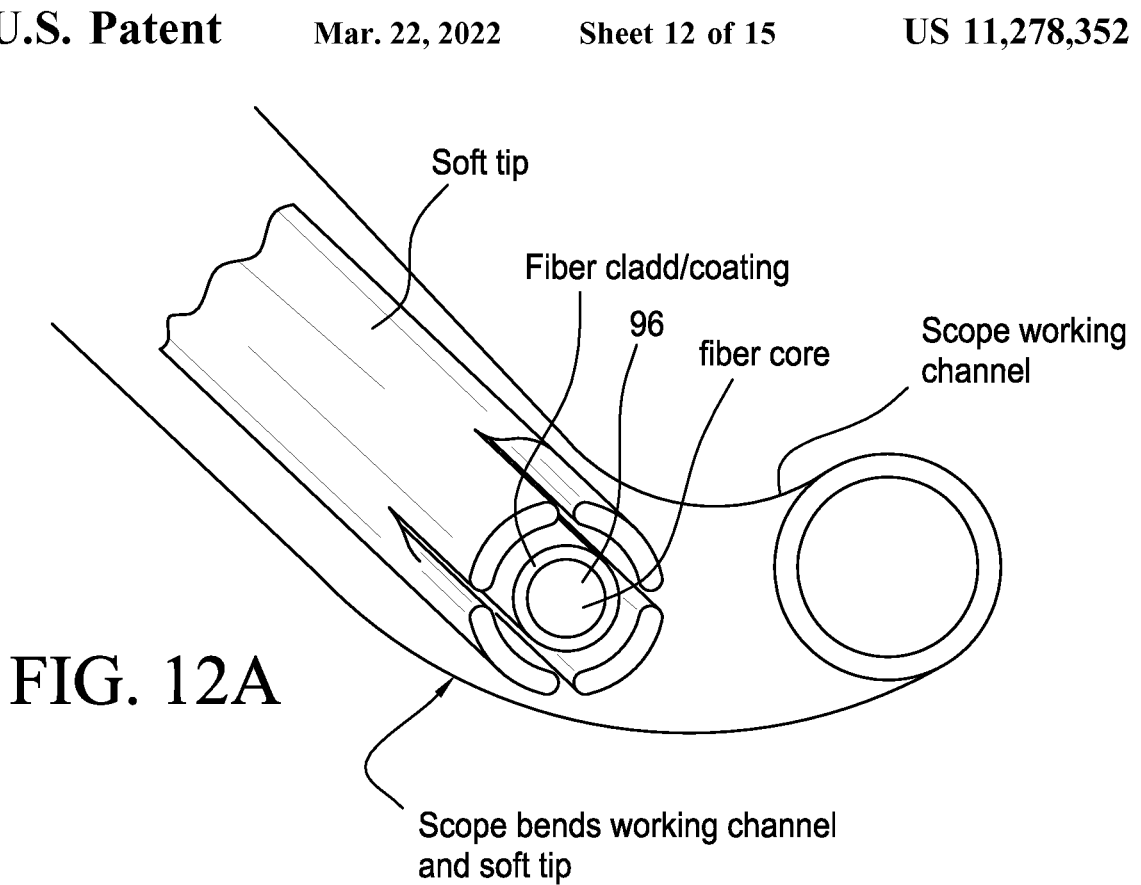
FIGS. 12A and 12B illustrate an implementation of the first preferred embodiment described in connection with in FIGS. 1 to 9D, in which phosphors are included in the soft tip to detect withdrawal of the fiber tip into a bent scope.
Figure 12B:
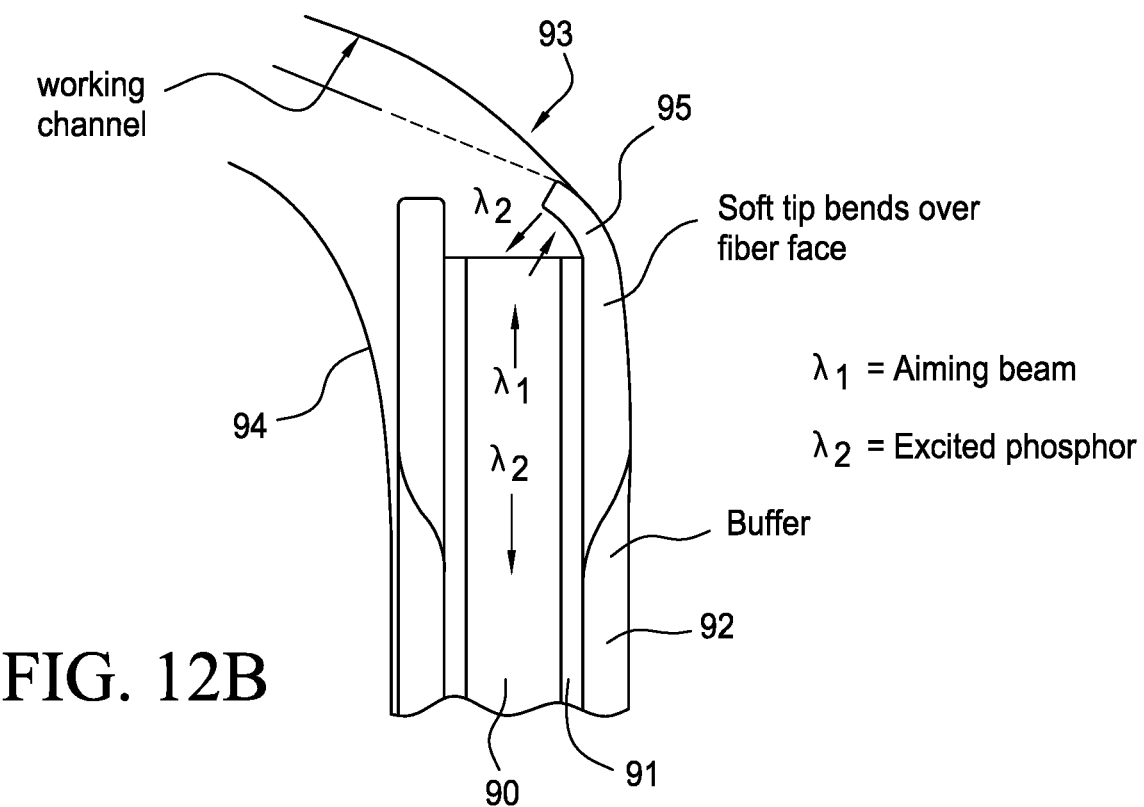

When phosphors are added to the soft tip, the soft tip can also be used to prevent damage caused by withdrawal of the fiber into a bent scope, by detecting that withdrawal into the bent scope has occurred, as can be understood from FIGS. 12A and 12B, which show a fiber that includes a core 90, cladding/coating 91, and buffer 92 as it approaches a bend 93 in scope 94. As illustrated above, the distal end of the buffer 92 has been replaced by a soft tip 95, to which phosphors have been added. The soft tip 95 may optically include slots 95 to facilitate bending, although it is possible to arrange for the soft tip to bend even without being slotted. When the soft tip 95 encounters the bend in the scope, it is deflected into the path of an aiming beam of wavelength $\lambda 1$, exciting the phosphors and causing them to emit light at wavelength $\lambda 2$, which can be detected either by a detector of by direct observation by the clinician.

Although the multiple-use soft tip of the embodiments illustrated in FIGS. 1-12, provide a number of advantages, it is also possible to provide single use or self-destructing fiber tips to protect the scope during insertion of the fiber, and/or to provide at least some tip erosion protection or reduction, according to a second preferred embodiment of the invention illustrated in FIGS. 13-16.

Figure 13:
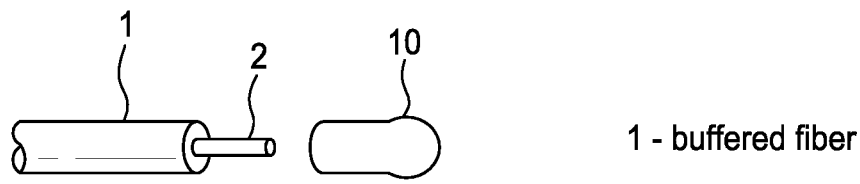
FIG. 13 shows an optical fiber and single-use cap constructed in accordance with the principles of a second preferred embodiment of the invention.

For example, as illustrated in FIG. 13, a buffered optical fiber 1 of the type conventionally used in surgical laser treatment procedures, such as stone removal or BPH, and which has optionally been stripped at the distal end to expose core and/or cladding, may be provided with a single-use protective cap 10 in the form of a sleeve arranged to fit over a front tip portion of the optical fiber 1 to protect the scope during insertion of the fiber, and to dissolve upon contact with bodily fluids or be blown off during lasing.

Figure 14:
FIG. 14 shows the manner in which the single-use cap of FIG. 13 is assembled to the optical fiber before insertion into an introducer.

As illustrated in FIG. 14, the protective cap 10 is fitted over the stripped front portion of the fiber, before insertion of the fiber into an endoscope or other introducer.

Figure 15:
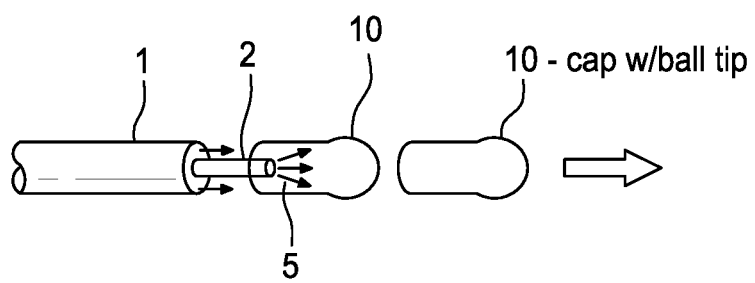
FIG. 15 illustrates removal of the single-use cap of FIGS. 13 and 14 upon firing off the laser during a treatment procedure.

FIG. 15 illustrates an alternative in which the single-use protective cap 10 is designed to be blown off the end of the fiber by radiation 5 during lasing. After being blown off the end of the fiber, the cap 10 will remain in the patient, and therefore is made of a material that will dissolve in an aqueous solution, so that the protective but will harmlessly dissolve and not pose a risk to the patient after removal. Suitable materials include bovine or vegetable based gelatin materials such as pullulan or hypromellose.

Figure 16:
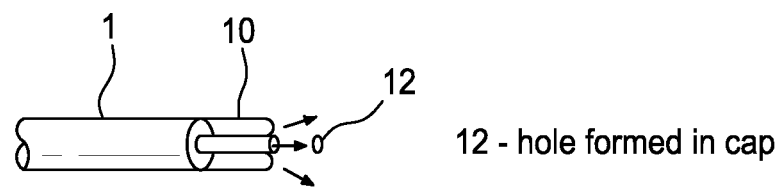
FIG. 16 illustrates a variation of the single-use cap of FIG. 15 in which a hole is formed in the single-use cap upon initial firing of the laser.

Alternatively, as shown in FIG. 16, the single-use protective cap 10 may remain on the end of the fiber after firing of the laser, but a portion of the cap in the path of the laser will be destroyed by being vaporized by the laser or ruptured by the pressure of rapidly expanding laser-heated vapor or fluids within the cap, forming a hole 12 through which the laser can pass without interference or obstruction during treatment. In this alternative embodiment, the single-use protective cap 10 may be made of a non-dissolvable material, although it can also still be made of a nontoxic dissolvable material if desired. In addition, the cap may include a pre-drilled or pre-formed hole in the path of the laser.

Figure 17A:
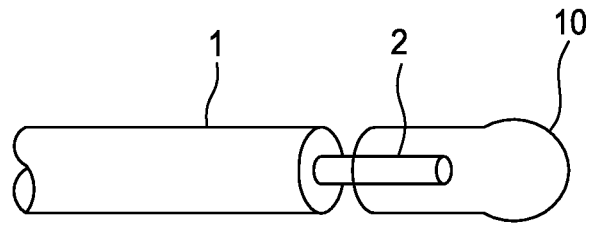
FIGS. 17A-17D illustrate alternative tip shapes for single-use fiber tips of the type illustrated in FIGS. 13-16.
Figure 17B:
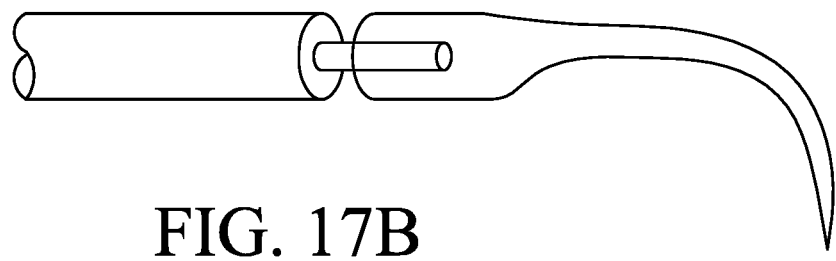
Figure 17C:
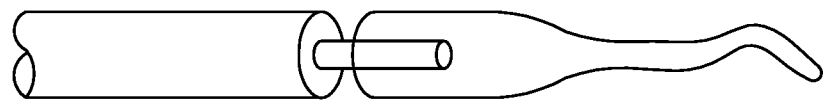
Figure 17D:
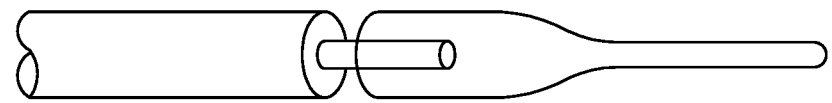
Figure 17E:
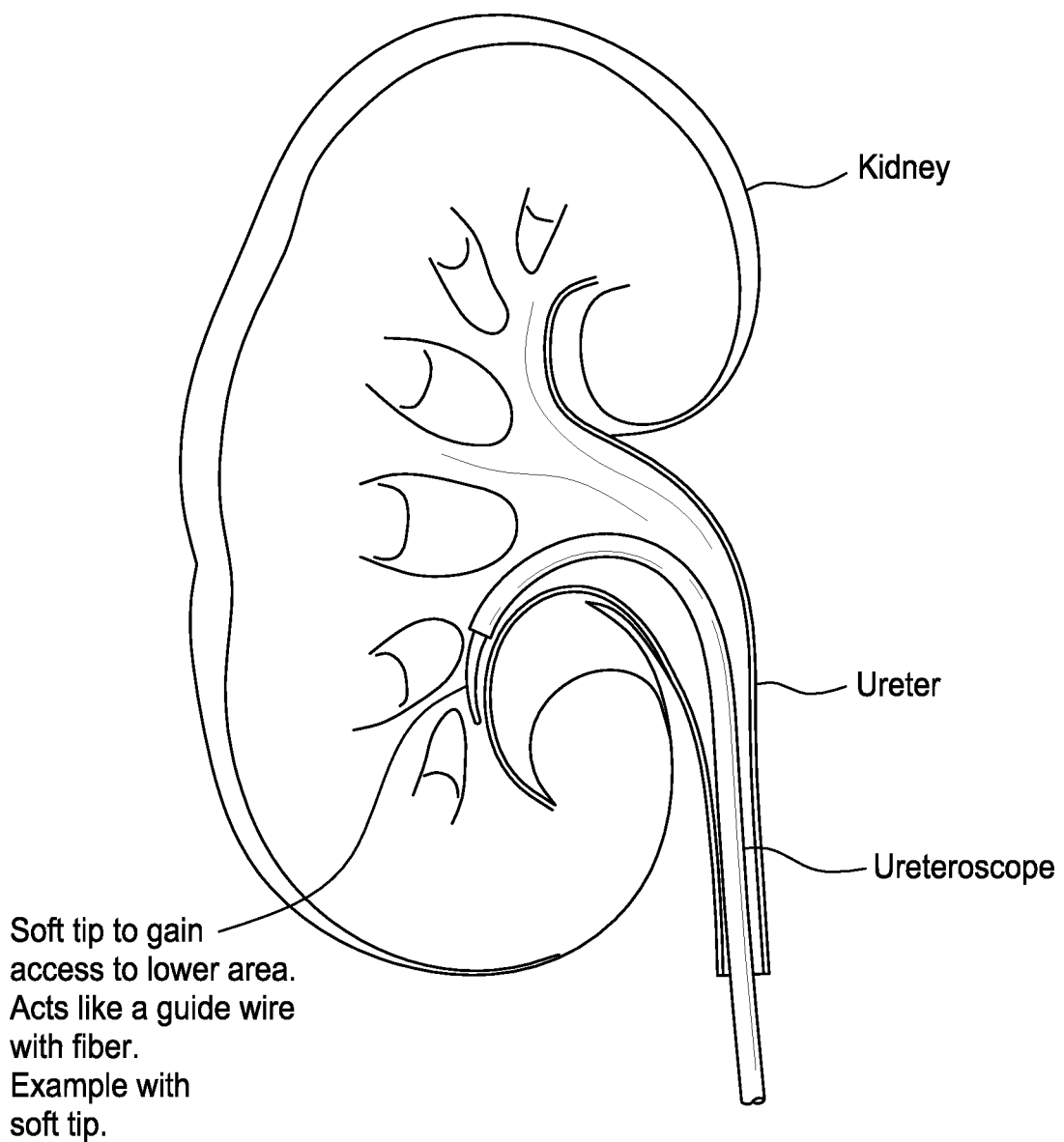
FIG. 17E shows an application of the tip shape illustrated in FIG. 17B.

The single-use cap 10 is illustrated in FIGS. 13-16 as having an expanded, rounded or partially spherical front end but it will be appreciated that the tip may be modified to have a variety of shapes, including the shapes illustrated in FIGS. 17A to 17E, all of which minimize scoring when the fiber is inserted into a scope. The curved tip shape shown in FIG. 17B has the added advantage that it may be used to guide the distal end of the fiber into areas of an organ, such as a kidney, that would otherwise require a guide ware, as is illustrated in FIG. 17E. Those skilled in the art will appreciate that the alternative tip shapes illustrated in FIGS. 17A-17E may also be applied to multiple-use tips or protective caps.

Figure 21:
FIG. 21 illustrate fiber end face shapes to which the principles of the present invention may be applied.
Figure 21:
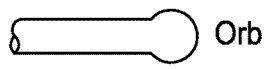
Figure 21:
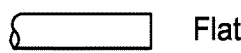
Figure 21:
Figure 21:
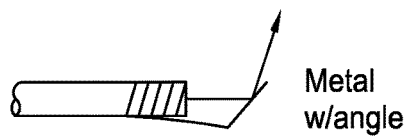
Figure 21:
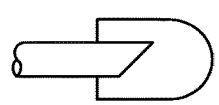
Figure 21:
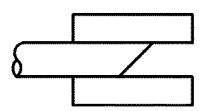

In addition, the single-use protective caps of this embodiment are not limited to end firing fiber applications. Instead, the single-use protective caps may be used with any of the fiber tips shown in FIG. 21, including side-firing angled tips, with or without a dielectric or metal coating, or added metal reflector.

Turning to FIGS. 18A-18C, 19, and 20, in embodiments where a single-use or reusable protective cap or tip as disclosed herein is combined or used with a sheath that extends from the protective cap or tip to a collar provided at the proximal end of the sheath, it may be desirable to also cover the portion of the fiber that extends from the proximal end of the sheath, in order to maintain sterility while changing the sheath or cap if it were to become damaged or fouled before during an surgical or treatment procedure. For this purpose, a drape may be provided. The drape may be similar in configuration to the Microtek™ coupler camera drape depicted in a video available on the website [[https://]]youtube/SakMmEpF2c4, which is arranged to allow changing optics during surgical procedures, but in the present embodiment is applied to the collar at the proximal end of the fiber sheath.

Figure 18A:
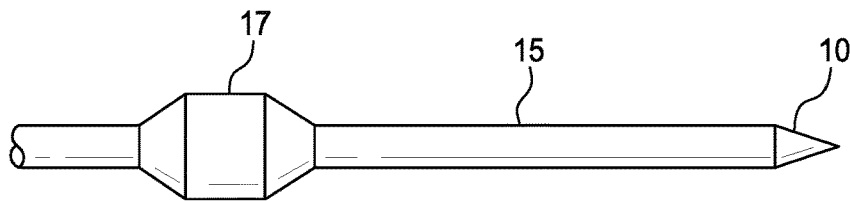
FIGS. 18A-18C respectively show a fiber, a protective cap and sheath, and a drape that may be used together according to another preferred embodiment of the invention.
Figure 18B:
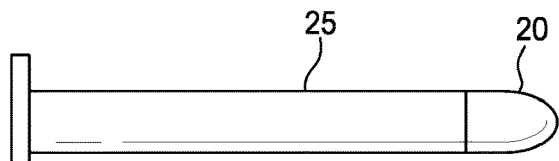
Figure 18C:
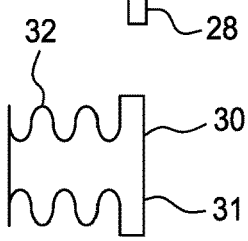
Figure 19:
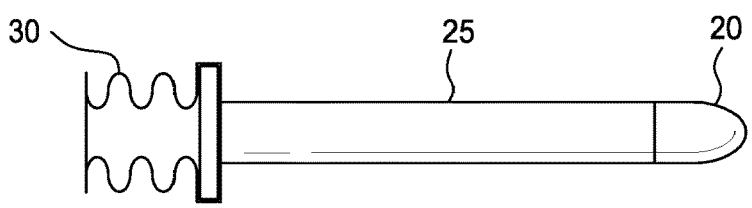
FIG. 19 shows a combination of the protective cap/sheath of FIG. 17B and the drape of FIG. 18C.
Figure 20:
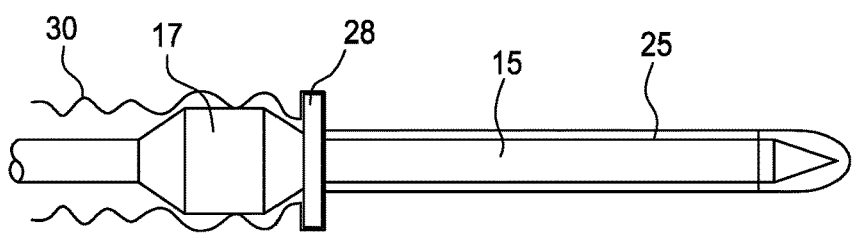
FIG. 20 shows the manner in which the drape of FIGS. 17C and 18 is extended over a proximal end of the fiber.

FIGS. 18A to 18C respectively show an optical fiber 15, a reuseable fiber tip or sheath with a collar 28 at a proximal end and a transparent cap 20 at a distal end, a drape 30 having one end 31 that fits over the collar 28, as illustrated in FIG. 19, and a bellows-like main body section 32 that encloses a portion of the fiber 15 extending from the proximal end of the sheath 25 after the fiber 15 has been inserted into the sheath 15, as illustrated in FIG. 20.

The drape 30 may be adapted for use with different optical fibers and/or different sheath/protective tip configurations, including sheath configurations that lack a collar. For example, the fiber 15 illustrated in 18A includes a conical tip 10 and an optional handle 17 at a proximal end of the fiber to facilitate rotating or sliding of the fiber by a clinician during a surgical or treatment procedure. However, the fiber 15 may, by way of example and not limitation, utilize any of the different tip configurations illustrated in FIG. 19, including a cone, an orb, a flat tip, an angled tip, an angled tip with a dielectric coating, a tip that includes a metal layer or piece extending at an angle, an angled tip with an integral cap, and an angled tip within a protective tube. The sheath 25 and transparent cap 20 may also be varied, and may include transparent caps made of quartz, silica, Teflon, sapphire, or diamond, as well as tubular caps with an opening to provide fluid flow and or index matching.

Having thus described preferred embodiments of the invention, it will be appreciate that the above description is illustrative in nature, and that the invention is intended to be limited only by the appended claims.

What is claimed is:

1. A sleeve structure for an optical fiber,
wherein the optical fiber is configured to be inserted through a scope to deliver laser energy to a stone during a laser lithotripsy procedure,
wherein the sleeve structure comprises a protective section of soft resilient material that surrounds a fiber core and fiber cladding at a tip of the optical fiber to prevent erosion of an exposed face of the fiber tip during a laser lithotripsy procedure, and to protect a working channel of the scope from sharp edges during insertion of the fiber tip through the scope,
wherein the protective section of soft resilient material extends a predetermined distance beyond the exposed face of the fiber tip to prevent contact between the fiber tip and a stone, and
wherein the protective section of soft resilient material is cylindrical and includes a central bore that extends from a first end into which the fiber tip is inserted to a second end that faces the stone during the lithotripsy procedure.

2. A sleeve structure as claimed in claim 1, wherein the resilient material is a material of a buffer of the optical fiber.

3. A sleeve structure as claimed in claim 2, wherein the protective section of buffer material is a replacement section fitted over a stripped section of the optical fiber tip from which original buffer material has been removed, the replacement section of buffer material having an axial length that is greater than a length of the stripped section.

4. A sleeve structure as claimed in claim 3, wherein the replacement section of buffer material is secured to the optical fiber tip by a heat shrink sleeve.

5. A sleeve structure as claimed in claim 3, wherein the replacement section of buffer material includes a dopant that emits light when heated to a predetermined temperature.

6. A sleeve structure as claimed in claim 3, wherein an end of the replacement section of buffer material is flared to facilitate assembly of the replacement section to the stripped section of the optical fiber.

7. A sleeve structure as claimed in claim 2, wherein the protective section is cut from an original section of buffer material and slid axially by said predetermined length.

8. A sleeve structure as claimed in claim 7, wherein a gap formed by axially sliding the original section of buffer material is filled with an adhesive material.

9. A soft protective tip for an optical fiber used in a laser lithotripsy procedure, comprising a cylindrical structure made of a soft material and fixed to a distal end of a buffer or coating of the optical fiber, the soft protective tip extending between the distal end of the buffer or coating to at least a tip of the optical fiber that has been stripped of the buffer or coating, to thereby protect the working channel of a scope into which the optical fiber is inserted, from scoring or puncture by the fiber tip, and to protect an end face of the optical fiber from erosion during the laser lithotripsy procedure,
wherein the soft protective tip further extends beyond the end face of the optical fiber, and
wherein a central bore of the cylindrical structure forms a passage for laser energy that extends from the end face of the optical fiber to a distal end of the cylindrical structure, the distal end of the cylindrical structure facing a targeted stone during the laser lithotripsy procedure.

10. A soft protective tip as claimed in claim 9, wherein a material of the soft protective tip is PTFE or ETFE.

11. A soft protective tip as claimed in claim 9, wherein the soft protective tip is secured to the buffer optical fiber by a press fit.

12. A soft protective tip as claimed in claim 9, wherein the soft protective tip is adhered to the buffer or coating by glue or welding.

13. A soft protective tip as claimed in claim 9, wherein the soft protective tip is adhered to the buffer or coating by being threaded onto an externally threaded end of the buffer or coating.

14. A soft protective tip as claimed in claim 9, wherein a material of the soft protective tip is transparent and visually distinguishable from a material of the buffer or coating.

15. A soft protective tip as claims in claim 9, wherein the stripped tip of the fiber is further enclosed within an additional plug.

16. A soft protective tip as claimed in claim 15, wherein the additional plug is made of PTFE or ETFE.

17. A soft protective tip as claimed in claim 9, wherein a distal end of the soft protective tip has a reduced thickness to increase flexibility and enable a stone to be gripped by the soft protective tip so as to pin the stone to another tissue.

18. A soft protective tip as claimed in claim 9, wherein a material of the soft protective tip is doped to emit radiation when laser energy is incident on an inside diameter of the soft protective tip.

19. A sleeve structure for a tip of an optical fiber, comprising:
a generally cylindrical body having a central bore with two sections,
wherein a narrower one of the sections includes a first end that fits over a stripped core or cladding of the optical fiber and a second end that faces a stone during a laser lithotripsy procedure,
wherein a wider one of the sections fits over a buffer of the optical fiber,
wherein a shoulder between the narrower and wider sections limits insertion of the optical fiber into the sleeve structure such that a tip of the fiber is set back from an end of the sleeve structure such that the narrower one of the sections extends beyond an end face of the optical fiber,
wherein the optical fiber is configured to be inserted through a scope to deliver laser energy to the stone during the laser lithotripsy procedure, and
wherein during the laser lithotripsy procedure, the sleeve structure is compressed axially upon contact with a stone, thereby enabling a distal end of the optical fiber to also contact the stone or to be spaced a predetermined minimum distance from the stone.

* * * * *